United States Patent

Tanaka

[11] Patent Number: 5,596,991
[45] Date of Patent: Jan. 28, 1997

[54] CATHETER TYPE ULTRASOUND PROBE

[75] Inventor: Toshizumi Tanaka, Omiya, Japan

[73] Assignee: Fuji Photo Optical Co., Ltd., Omiya, Japan

[21] Appl. No.: 403,960

[22] Filed: Mar. 14, 1995

[30] Foreign Application Priority Data

Apr. 7, 1994 [JP] Japan .................................. 6-092912

[51] Int. Cl.⁶ ..................................................... A61B 8/12
[52] U.S. Cl. ....................................................... 128/662.06
[58] Field of Search .......................... 128/660.1, 662.06;
600/109, 127, 137, 149–150

[56] References Cited

U.S. PATENT DOCUMENTS 5,417,216  5/1995  Tanaka ................................ 128/660.1
5,464,016  11/1995  Nicholas et al. .................... 128/662.06

Primary Examiner—Francis Jaworski
Attorney, Agent, or Firm—Oblon, Spivak, McClelland, Maier & Neustadt, P.C.

[57] ABSTRACT

A catheter type ultrasound probe having an elongated flexible catheter and a controller for a rotational driver for the ultrasound transducer on the catheter member. The device includes a flexible sheathing tube closed at the fore end, a rotatable support member located in a tip end portion of the sheathing tube, an ultrasound transducer mounted on the rotatable support member and a flexible transmission shaft including at least a transmission coil having a series of intimately contacting helices. The flexible transmission shaft extends through the sheathing tube and is connected at the fore end to the rotatable support member. A rotational shaft is coupled to the other end of the flexible transmission shaft and is rotationally driven from the rotational driver on the controller. A pair of fore and rear stoppers located in the fore and rear end portions of the catheter retain the flexible transmission shaft in a tensioned state between predetermined head and tail end positions.

4 Claims, 4 Drawing Sheets

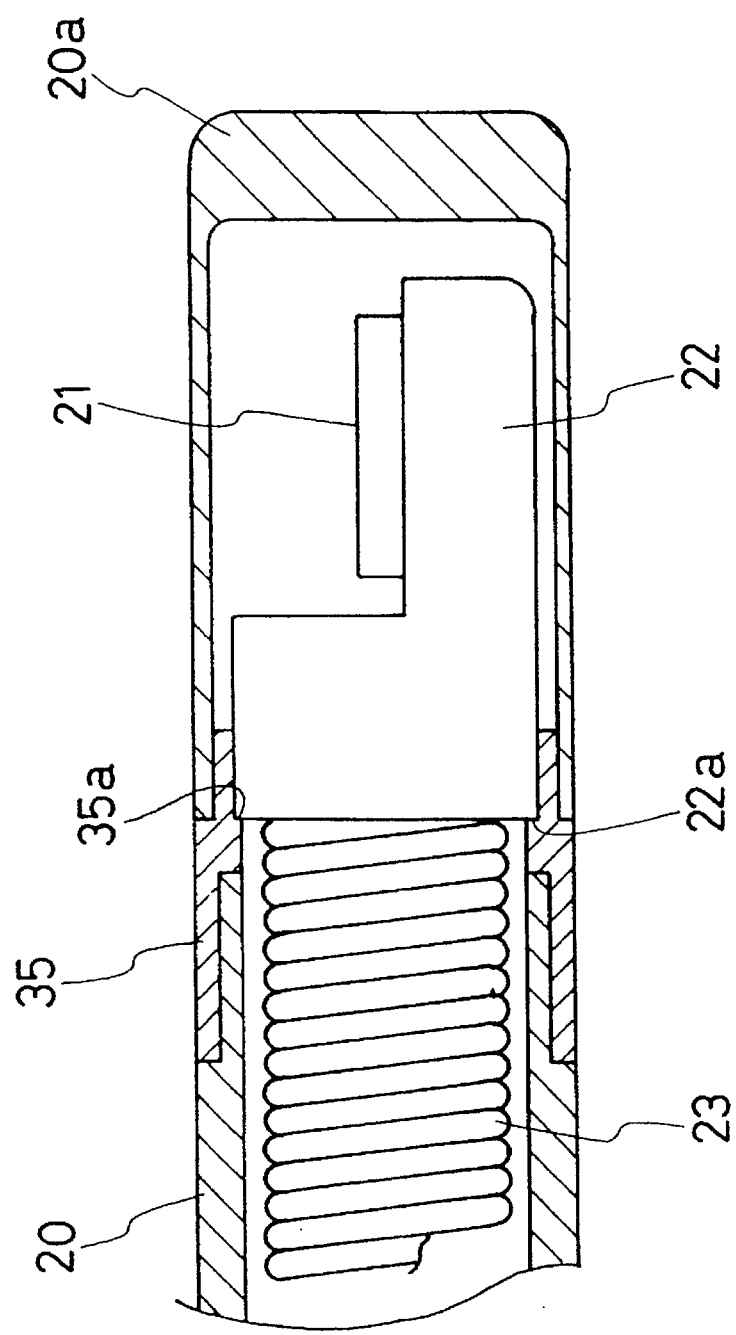

CATHETER TYPE ULTRASOUND PROBE

BACKGROUND OF THE INVENTION

1. Field of the Art

This invention relates to a catheter type ultrasound probe to be inserted into an intracavitary portion of a patient to make intracorporeal examinations by ultrasound scanning.

2. Description of the Prior Art

There have been known in the art the so-called catheter type ultrasound examination systems having an ultrasound transducer mounted on a tip end of a catheter member to be inserted into an intracavitary portion of a patient, to obtain a tomographic ultrasound image of a particular intracorporeal portion of interest by an ultrasound scanning operation moving the ultrasound transducer in a linear direction or in a rotational direction about the axis of the catheter member. The ultrasound internal examination systems of this sort are largely constituted by an elongated catheter member to be introduced into an intracavitary portion directly or indirectly through a guide means on an endoscope or the like, and a controller section with manipulating means to control the position of the transducer for the ultrasound scanning operation. In certain cases, a catheter member is integrally connected to a controller section. However, there are also separate type catheter members which are disconnectibly connectible to a controller section prior to use.

For the purpose of protecting the ultrasound transducer which is mounted on a distal end portion of the catheter member, it is the usual practice in the art to encase the catheter member in a sheathing in the form of a flexible tube, which has its distal end simply closed or closed with a closure cap with excellent acoustic properties, and to mount an ultrasound transducer on a cradle-like support plate within a fore end portion of the sheathing tube. In case of radial scanning, the ultrasound transducer is rotationally driven within the sheathing tube. In order to put the ultrasound transducer in rotation, the support plate which supports the transducer needs to be rotatable and connected to a rotation transmission member which is extended through the catheter member to the proximal end thereof. In case the catheter member is of the type which is integrally connected to the controller, the rotation transmission member is further extended into the controller and coupled with a rotational drive means such as electric motor or the like. On the other hand, in case the catheter member is of the separate type as mentioned above, the rotation transmission member is extended to a rotational coupling means at the proximal end of the catheter member, which is disconnectibly connectible to a drive source on the part of the controller. As far as the linear scanning operation is concerned, there is no need for driving the ultrasound transducer from the rotational drive source while the transducer is in a linear scanning operation. However, in order to control the angular position of the ultrasound transducer, it is necessary to provide a rotation transmission member which can turn the ultrasound transducer into a desired angular position prior to a linear scanning operation.

On the other hand, the catheter member should be capable of bending itself in an arbitrary direction along a path of insertion leading to an intracavitary portion to be examined. The sheathing tube of the catheter member, which is formed of a flexible material, can bend itself along turns or bends in the path of insertion. In this regard, the rotation transmission member which is encased in the flexible sheathing tube should also have a suitable degree of flexibility. This requirement for the rotation transmission member can be suitably met by a flexible shaft which is constituted by a transmission coil or coils each consisting of a series of tightly contacting helices in the longitudinal direction thereof.

In order to transmit rotation accurately to the ultrasound transducer by the use of a rotation transmission member in the form of such a flexible shaft or the like, it is necessary to provide a certain degree of dimensional differential between the inside diameter of the sheathing tube and the outside diameter of the rotation transmission member to reduce to a minimum the friction resulting from the sliding contact between these two parts. No matter whether the catheter member is introduced into an intracavitary portion by direction insertion or by indirect insertion, for example, under the guidance of a biopsy channel of an endoscope, it is invariably required to bend its body along a path of insertion. When the catheter member is bent into a loop-like form, for example, the rotation transmission member within the sheathing tube is forced into a deviated position to abut against the inner periphery of the sheathing tube on the inner side of the loop. This deviation of the rotation transmission member tends to shift the position of the trandsucer support plate, moving same in a direction axially forward of the sheathing tube. As a result, the ultrasound transducer is pressed against the distal end face of the sheathing tube and forcibly rotated in frictional sliding contact with the sheathing tube. This frictional sliding contact with the sheathing tube is impedimental to smooth rotation of the ultrasound transducer and has possibilities of causing irregularities in rotational movement of the transducer especially in radial scanning operations.

To cope with this problem, prior art ultrasound probes usually have the fore distal end of the sheathing tube extended axially forward beyond the position of the ultrasound transducer within the sheathing tube in a sufficient degree for keeping the transducer and its support member out of contact with the interior surfaces of the sheathing tube even when the catheter member is bent into an arcuate shape. In this connection, it should be considered that the catheter members of ultrasound probes generally have a lengthy body ranging from about 1 m to about 2.5 m in length depending upon the position of the intracorporeal portion to be examined. Therefore, even if the dimensional differential between the inside diameter of the sheathing tube and the outside diameter of the rotation transmission member is held to a minimum value which would not impair smooth rotation, it is necessary to locate the ultrasound transducer normally in a retracted position at a distance of more than 10 mm and, on the safe side, more than 20 mm from the fore distal end of the sheathing tube when the catheter member is in a rectilinearly stretched state.

However, in case the catheter member is arranged to have the fore distal end of the sheathing tube extended forward largely beyond the position of the ultrasound transducer, difficulties are often encountered in making a scan along an intracavitary wall of complicate configuration where the fore end of the sheathing tube is very likely to come into abutment against a rising portion of the intracavitary wall, which blocks the scanning of the intracavitary wall portions between the fore end of the protruded sheathing tube and the retracted mount position of the ultrasound transducer. Besides, in case the catheter member is introduced into an intracavitary portion through a biopsy channel of an endoscope, the ultrasound probe needs to be manipulated with the aid of images of the endoscopic observation system in positioning the ultrasound transducer in face to face relation with an intracorporeal portion to be examined by the ultrasound probe. However, on such an occasion, what one can see through the endoscopic observation mechanism is simply the outer configuration of the fore end of the sheathing tube protruded out of the biopsy channel, failing to check the exact position of the ultrasound transducer within the sheathing tube. For this reason, if the ultrasound transducer position is easily shifted in the axial direction within the sheathing tube, it becomes difficult to locate the transducer correctly in face to face relation with an intracorporeal portion to be examined by the ultrasound probe, or to grip the exact position of an intracorporeal portion which is being examined.

SUMMARY OF THE INVENTION

With the foregoing situations in view, it is a primary object of the present invention to provide a catheter type ultrasound probe having an ultrasound transducer mounted at the tip end of a catheter member in such a manner as to prevent axial shifts of the ultrasound transducer position within a sheathing tube of the catheter member.

It is another object of the present invention to provide a catheter type ultrasound probe which can maintain an ultrasound transducer in a constant position within a tip end portion of a sheathing tube of a catheter member free of axial shifts and without hindering transmission of rotation to the ultrasound transducer even when the catheter member is bent into an angular or arcuate shape.

In accordance with the present invention, the above-stated objective is achieved by the provision of a catheter type ultrasound probe including an elongated flexible catheter member having an ultrasound transducer mounted at the tip end thereof and a controller having a rotational drive means for the ultrasound transducer, characterized in that the catheter member essentially includes: a flexible sheathing tube closed at the fore end thereof; a rotatable support member located in a tip end portion of the sheathing tube; an ultrasound transducer mounted on the rotatable support member; a flexible transmission shaft constituted by at least a transmission coil consisting of a series of intimately contacting helices, the flexible transmission shaft being extended through the sheathing tube and connected at the fore end thereof to the rotatable support member; a rotational shaft coupled with the rear end of the flexible transmission shaft and rotationally driven from the rotational drive means on the controller; and a couple of stopper means located in fore and rear end portions of the catheter member to retain the flexible transmission shaft in tensioned state between predetermined head and tail end positions.

The above and other objects, features and advantages of the invention will become apparent from the following description, taken in conjunction with the accompanying drawings which shows by way of example a preferred embodiment of the invention.

BRIEF DESCRIPTION OF THE DRAWINGS

In the accompanying drawings:

FIG. 4 is a sectional view on an enlarged scale of a rigid fore end section of the catheter member.

DESCRIPTION OF PREFERRED EMBODIMENTS

Hereafter, the invention is described more particularly by way of its preferred embodiments with reference to the accompanying drawings. In the following description, the invention is embodied by an ultrasound probe with a catheter member which is disconnectibly connectible to a controller and which is introduced into an intracavitary portion by way of a biopsy channel of an endoscope. However, it is to be understood that the invention is not limited to ultrasound probes of this type and can be applied to other ultrasound probes, for example, to an ultrasound probe with a catheter member to be directly introduced into an intracavitary portion of a patient or to an ultrasound probe with a catheter member integrally connected to a controller. Further, the invention is applicable to other than a radial scan type ultrasound probe as in the particular embodiment shown below. For example, the invention is likewise applicable to ultrasound probes with a linear scan type transducer.

Figure 1:
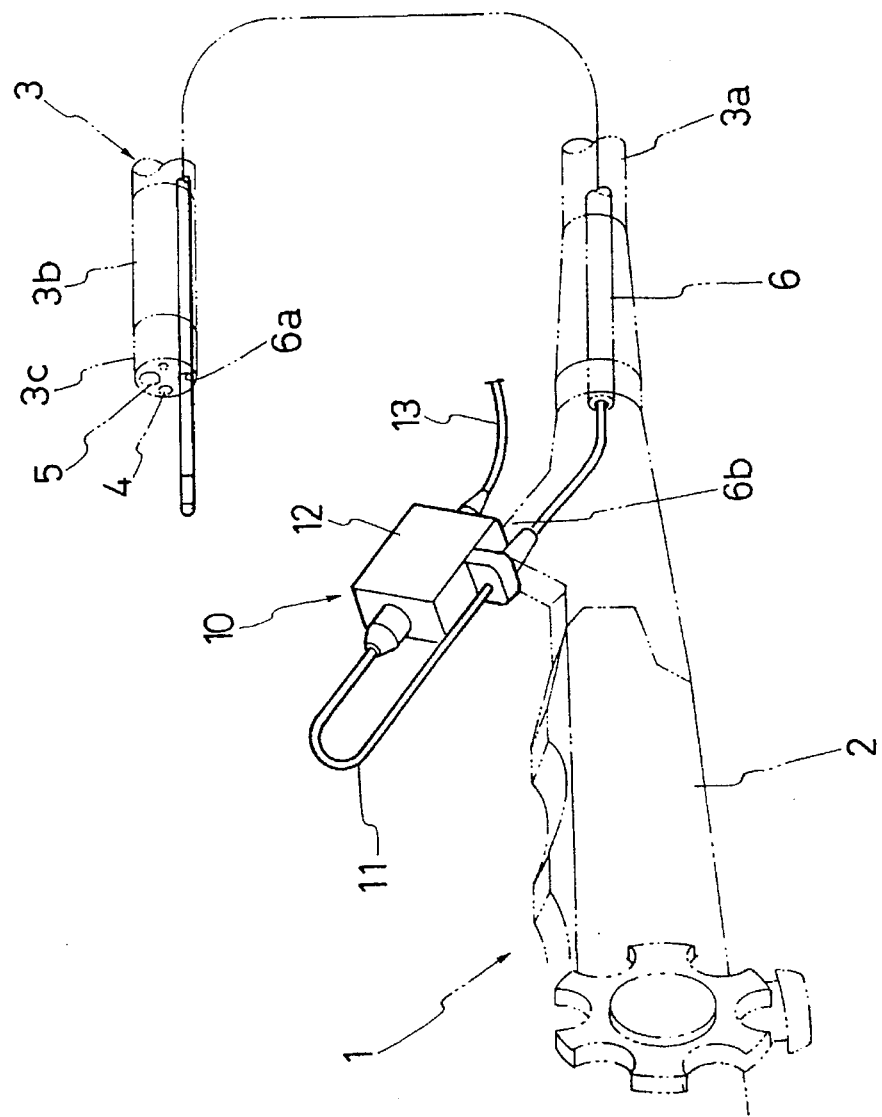
FIG. 1 is a fragmentary schematic view of an ultrasound probe according to the present invention, which is inserted in a biopsy channel of an endoscope.

Referring to FIG. 1, there is shown an ultrasound probe according to the invention, which is inserted in an endoscope. In this figure, designated at 1 is the endoscope which is largely constituted by a main body 3 with endoscopic control means, and an elongated insert portion 2 extended from the main body 2 for insertion into an intracavitary portion of a patient. The insert portion 3 is provided with an endoscopic observation means at its distal end, including an illumination window 4 and an observation window 5. Provided through the main body 3 and insert portion 2 of the endoscope 1 is a biopsy channel 6 through which forceps or other instrument can be introduced into an intracavitary portion under observation. The biopsy channel 6 has an exit opening a on the distal end face of the insert portion 2 in the vicinity of the afore-mentioned illumination window 4 and endoscopic observation window 5.

Indicated at 10 is an ultrasound probe which is largely constituted by a catheter member 11 and a controller 12 with manipulating control means for the probe. The catheter member 11 is disconnectibly connected at its proximal end to the controller 12 which is in turn detachably mounted on an entrance opening 6b of the biopsy channel 6 on the main body 2 of the endoscope 1. Led out from the controller 12 is a signal line cable 13 which is connected to an ultrasound image observation terminal (not shown).

Figure 2:
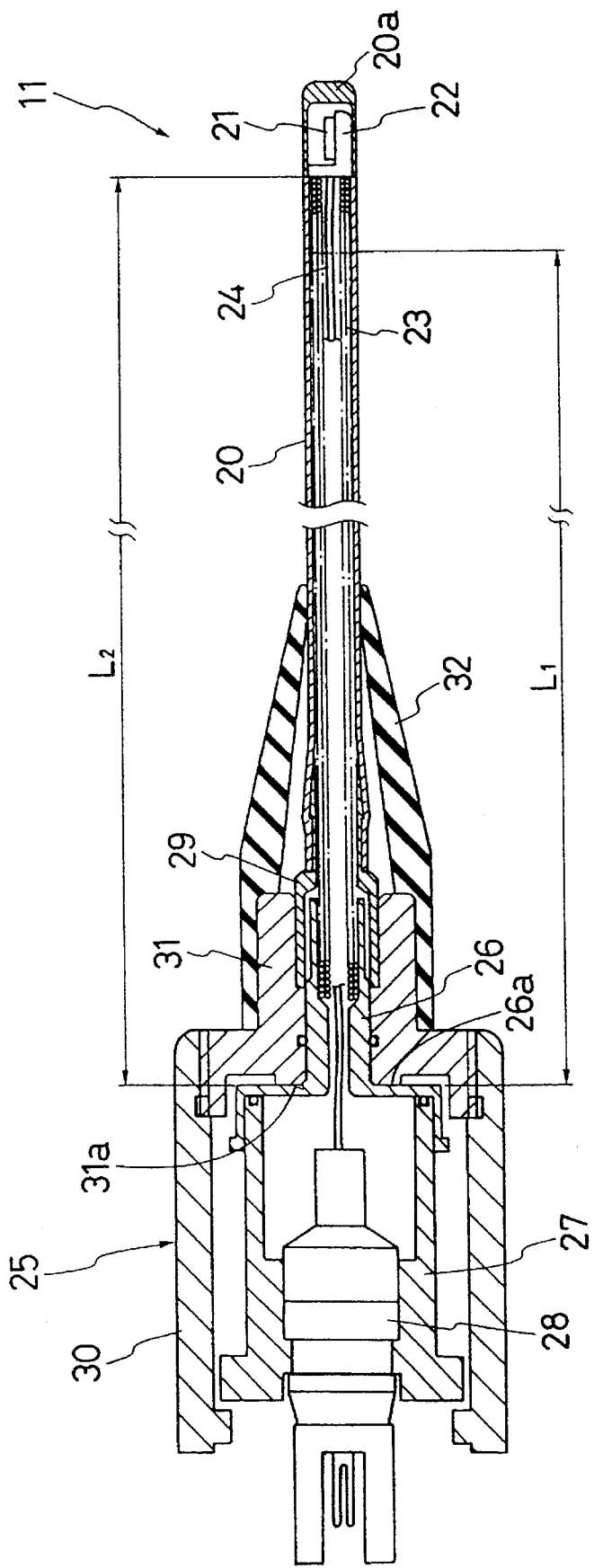
FIG. 2 is a longitudinal section of a catheter member of the ultrasound probe.
Figure 3:
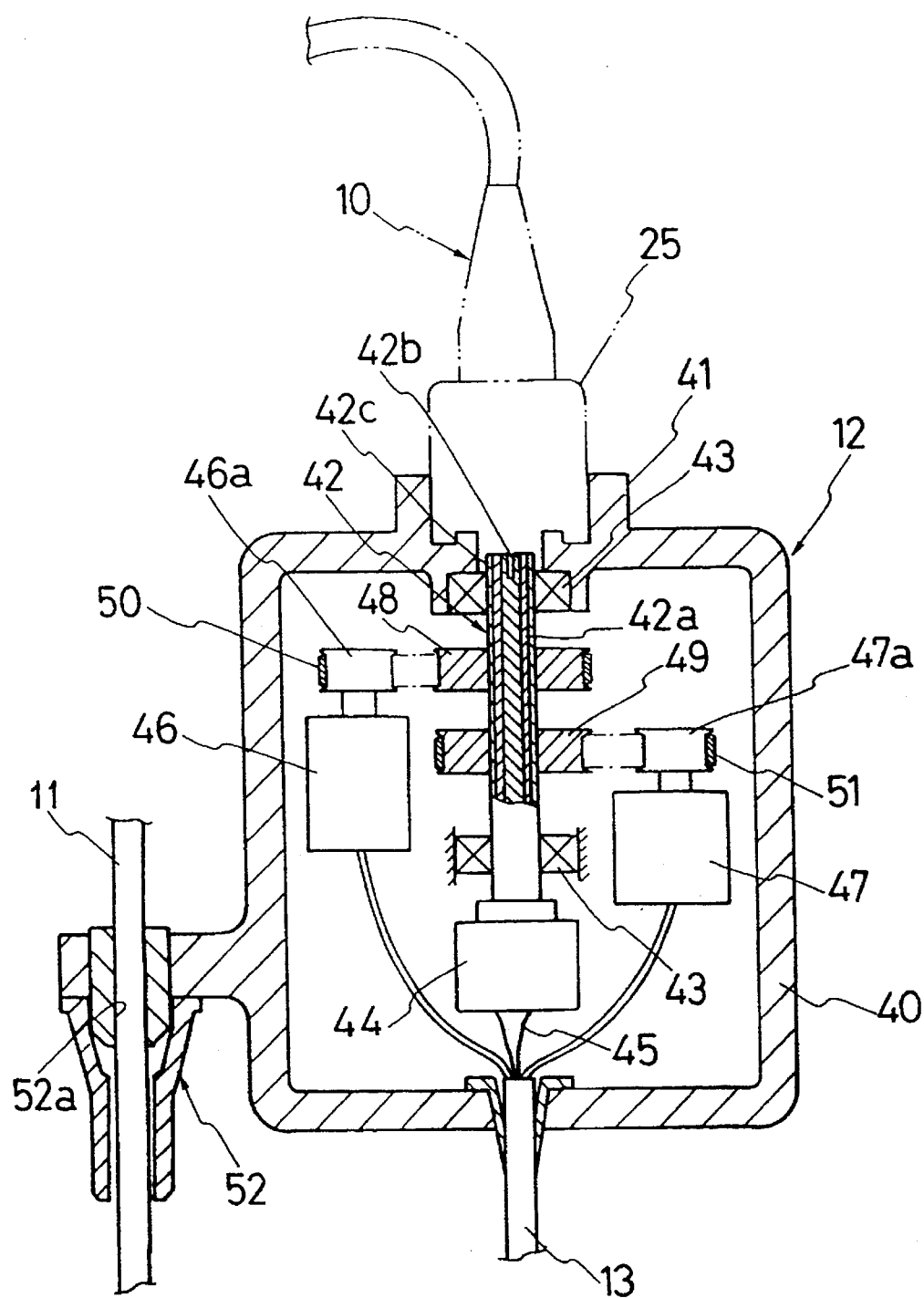
FIG. 3 is a sectional view of a controller of the ultrasound probe.

FIGS. 2 and 3 show in greater detail the arrangements of the catheter member 11 and the controller 12, respectively. The catheter member 11 is sheathed in a soft and flexible tube 20 of an electrically insulating synthetic resin material. The fore end of the sheathing tube 20 is closed with an end cap 20a of a material with excellent acoustic properties along with satisfactory shape-retaining properties. An ultrasound transmissive medium is sealed in the end cap 20a, which end cap houses therein an ultrasound transducer 21 which is mounted on a rotatable support member 22 in a fore end portion of the soft and flexible sheathing tube 20. The rotatable support member 22 is connected to the fore end of a flexible transmission shaft 23 which is composed of a couple of layers of transmission coils of metal wires each consisting of a series of intimately contacting helices. These transmission coils in the outer and inner layers consist of helices of opposite directions, so that a rightward or leftward rotation can be securely transmitted to the distal end of the flexible shaft when its proximal end is turned in a rightward or leftward direction. Therefore, the rotatable support member 22 on which the ultrasound transducer 21 is mounted can be rotationally driven in either direction through the flexible transmission shaft 23. Passed through the flexible shaft 23 is a signal line cable 24 which is connected at its fore end to the ultrasound transducer 21. Although the flexible transmission shaft 23 is constituted by a couple of layers of transmission coils in the particular embodiment shown, it may be constituted by a single layer of the transmission coil in case the ultrasound transducer is turned in one direction or by transmission coils arranged in triple or more layers or by transmission coils each consisting of a plural number of metal wires helically wound in a parallel relation with each other or in multiple layers.

The catheter member 11 is provided with a connector 25 at its proximal end to be disconnectibly connected to the controller 12. This connector 25 is largely constituted by a rotary part and a stationary part. The flexible transmission shaft 23 is fixedly secured to a rotary barrel 26 of a stepped cylindrical shape which is in turn coupled with a cylindrical retainer barrel 27. The signal cable 24 from the ultrasound transducer 21 is connected to a rotating electrode assembly 28 which is embraced in the retainer barrel 27. On the other hand, the flexible sheathing tube 20 is securely fitted in a sleeve member 29. The just-mentioned sleeve member 29 is in turn fixedly secured to a cylindrical connecting shell member 31 which is in turn fixedly threaded into a cylindrical outer shell member 30. Fixedly fitted on the connecting shell member 31 is a rubber sleeve 32 which is extended over a proximal end portion of the flexible sheathing tube 20 of the catheter member 11 to prevent same from bending or buckling to an excessive degree at the proximal end portion. Accordingly, the rotary barrel member 26 which is connected to the flexible transmission shaft 23 constitutes the rotary part of the connector 25 together with the cylindrical retainer barrel member 27 and the rotating electrode 28, while the sleeve 29 which is connected with the flexible sheathing tube 20 constitutes the fixed or stationary part together with the connecting shell member 31 and the outer shell member 30.

To permit connection of the catheter member 11, the controller 12 is provided with a connection terminal 41 on its housing 40, which can be coupled with the connector 25 on the part of the catheter member 11 in such a manner as to block rotation of the outer shell member 30 of the connector 25. Disposed in the connection terminal 41 is a rotary body 42 which is detachably connectible to the rotating electrode assembly 28. The rotary body 42 has a cylindrical core electrode 42b and a sleeve-like outer electrode 42c concentrically on the inner and outer sides of an insulating member 42a. The rotating electrode assembly 28 is provided with a split pin electrode 28a and a notched tubular electrode 28b to be electrically connected with the core electrode 42b and the outer electrode 42c of the connection terminal 41 on the rotary body 42, respectively, when the rotating electrode assembly 28 is coupled with the latter. In the coupled state, the rotating electrode assembly 28 is locked to the rotary body 42 to follow the rotation of the latter in a secure manner. Therefore, although not shown in the drawings, key and keyways or other suitable locking means are provided between circumferential surfaces of the rotary body 42 and the rotating electrode assembly 28 to block their relative rotations.

The rotary body 42 is rotatably supported within the housing 40 through bearings 43, and, at the other end away from the connection terminal 41, it is coupled through fluid contacts, brush contacts, slip rings or the like with a fixed socket 44 which is connected to signal lines 45 of the cable 13 from the ultrasound image observation terminal. Consequently, the cable. 24 which is passed through the flexible shaft 23 for rotation therewith is electrically connected with the signal lines 45 of the non-rotatable cable 13 through the rotating electrode assembly 28, rotary body 42 and the fixed socket 44.

The rotational drive source for driving the flexible transmission shaft 23 includes an electric motor 46 and an encoder 47 which are mounted on the controller housing 40, and a couple of pulleys 48 and 49 which are provided on the rotary body 42 to be coupled with the rotating electrode assembly 28. These pulleys 48 and 49 on the rotary body 42 are rotationally linked to output shaft 46a of the motor 46 and input shaft 47a of the encoder 47 by way of transmission belts 50 and 51, respectively. Accordingly, upon starting the motor 46, the rotary body 42 is put in rotation and the rotational angle of the rotary body 42 is simultaneously detected by the encoder 47.

The controller 12 is detachably mounted on the entrance opening 6b of the biopsy channel 6 of the endoscope. For this purpose, the controller 12 is provided with a pipe-like connector nose 52 to be fitted into the entrance opening 6b, the connector nose 52 internally providing a passage 52a for passing therethrough the proximal end portion of the catheter member 11 which connected to the controller 12. Accordingly, the controller 12 can be fixedly and detachably mounted in position on the endoscope upon fitting the connector nose 52 into the entrance opening 6b of the biopsy channel 6. The catheter member 11 in the passage 52a of the connector nose 52 can be pushed in a forward or backward direction to adjust the extension length of the fore end portion of the catheter member 11 to be protruded from the exit opening 6a of the biopsy channel 6 at the distal end of the endoscope.

In order to use the ultrasound probe of the above-described arrangements for an intracorporeal examination, firstly the insert portion 3 of the endoscope 1 is introduced into an intracavitary portion, and then the catheter member 11 of the ultrasound probe 10 is inserted into the biopsy channel of the endoscope 1, followed by fixation of the connector nose 52 of the controller 12, which holds the proximal end portion of the catheter member 11, on the entrance opening 6b of the biopsy channel 6. As soon as the insert portion 3 of the endoscope 1 reaches an intracavitary portion of interest, the catheter member 11 of the ultrasound probe 10 is protruded from the exit opening 6a of the biopsy channel 6 over a suitable extension length.

In this state, the motor 6 on the controller 12 is actuated to put the rotary body 42 in rotation. This rotation of the rotary body 42 is transmitted to the rotary barrel member 26, which is connected to the flexible transmission shaft 23, through the rotating electrode assembly 28 and the retainer barrel member 27. As a result, the rotation of the rotary barrel member 26 is transmitted to the flexible transmission shaft 23 to put the latter in rotation about its axis, thereby rotationally driving the ultrasound transducer 21 on the rotatable support member 22 which is connected to the fore end of the flexible transmission shaft 23. In this connection, if an ultrasound transmissive medium with suitable lubricative properties is sealed in the flexible sheathing tube 20, it contributes to reduce the friction of sliding contact between the rotating flexible shaft 23 and the inner surface of the flexible sheathing tube 20 to a certain degree to ensure smoother rotation of the ultrasound transducer.

With the above-described arrangements, the ultrasound transducer 21 is rotated in step with the rotary body 42, the rotational angle of which is detected by the encoder 47. Therefore, on the basis of output signals of the encoder 47, ultrasound pulses are transmitted into intracorporeal regions from the ultrasound transducer 21 through the end cap 20a at predetermined angular intervals in rotation. The return echoes from intracorporeal tissues in the tomographic area of examination are received by the ultrasound transducer 21 and transferred to the ultrasound image observation terminal through the signal cable 24 via the rotating electrode assembly 28 and rotary body 42 and then through the fixed socket 44 and cable 45. As well known in the art, the received echo signals are converted into video signals through predetermined signal processing operations at the ultrasound image observation terminal to display ultrasound images of the scanned area on a monitor screen.

With regard to the ultrasound scanning operation, the rotatable support member 22, which supports the ultrasound transducer 21, needs to be located within the flexible sheathing tube 20 at a position as close to the fore end of the sheathing tube 20 as possible in order to make an ultrasound scan at any arbitrary position and to make it easier to confirm the position of the ultrasound transducer 21 through the observation window 5 of the endoscope. For this purpose, the ultrasound transducer 21 should be located and constantly retained in a position in the extreme proximity of the fore distal end of the sheathing tube 20 despite the flexing movements of the catheter member 11.

In order to meet these requirements according to the present invention, a stopper ring 35 is provided at the joint of the end cap 20a with the sheathing tube 20. The stopper ring 35 is formed to have an inner diameter smaller than the outside diameter of the rotatable support member 22, so that the end face of the support member 22 on the proximal side of the catheter member is abutted against the opposing face of the stopper ring 35 to fix the position of the rotatable support member 22 in the axial direction of the flexible sheathing tube 20. On the other hand, the rotatable barrel member 26 which is directly connected to the flexible shaft 23 is abutted against the connecting shell member 31 on the stationary side of the connector 25. Further, the flexible transmission shaft 23 of the catheter member 11, to be stretched between the rotatable support member 22 and the rotatable barrel 26, is arranged to make a length $L_1$ in a free detached state, which falls short of the length $L_2$ of the flexible sheathing tube 20 between the fore end face of the stopper ring 35 and the rear end face of the connecting shell member 31 in abutting engagement with shoulder portions of the inner rotary barrel member 26. As a consequence, the rear end face 22a of the rotatable support member 22 and the shoulders 26a of the rotary barrel member 26 act as stoppers for the opposite ends of the flexible transmission shaft 23 in cooperation with the end face 35a of the stopper ring 35 and the end face 31a of the connecting shell member 31.

With the above-described arrangements, the flexible transmission shaft 23 is fitted in and stretched through the flexible sheathing tube 20 in a slightly tensioned state. In this instance, the dimensional differential between the length $L_1$ of the flexible shaft 23 and the length $L_2$ of the sheathing tube 20 is set at a value which is greater than the length over which the flexible transmission shaft 23 tends to shift in a forward direction within the flexible sheathing tube 20 when the catheter member 11 is bent along a path of insertion or while insertion through the biopsy channel 6 of the endoscope 1. For example, in case the endoscope is a gastroscope, its insert portion is introduced into the stomach through the oral cavity and the esophagus via the throat where the insert portion has to be turned at a large angle. Therefore, in consideration of the extent of bending of the catheter member 11 at such a large turn which exists in the path of insertion, the length of the flexible transmission shaft 23 is differentiated from that of the flexible sheathing tube 20 to a degree which is greater than a possible forward axial shift in position which might occur to the flexible transmission shaft within the sheathing tube 20 as a result of the bending movement. Generally speaking, the stretching of the flexible shaft 23 less than 1% of its overall length is sufficient for this purpose, provided the dimensional differential between the inside diameter of the flexible sheathing tube 20 and the outside diameter of the flexible transmission shaft 23 is held to a minimum possible value which would not hinder smooth rotation of the flexible shaft 23 within the sheathing tube 20.

Consequently, when the catheter member 11 is bent along a turn in the path of insertion to such a degree as would normally cause an axial displacement of the flexible shaft 23 within and along the inner surface of the bent sheathing tube 20, this tendency of axial displacement or shift is absorbed by contraction of the flexible transmission shaft 23 itself. Accordingly, the end face 22a of the rotatable support member 22 at the fore end of the flexible transmission shaft 23 is abutted against the opposing end face 35a of the stopper ring 35 instead of being pushed forward by the flexible shaft 23. Therefore, there will be no possibilities of the rotatable support member 22 getting into abutting engagement with the distal end face of the flexible sheathing tube 20 even in a case where the rotatable support member 22 is located in a position in the extreme proximity to the end cap 20a of the sheathing tube 20. It follows that, as long as a tip end portion of the catheter member 11 is protruded to a certain extent from the exit opening 6a of the biopsy channel 6, it becomes possible to make an ultrasound scan by the use of the ultrasound transducer 21 which is constantly held in position substantially at the distal end of the protruded catheter member 11, even through an intracavitary wall with a complicate profile which would otherwise make the ultrasound scanning infeasible by limiting the length of protrusion of the catheter member 11. Besides, the position of the ultrasound transducer 21, which is constantly located at the distal end of the catheter member 11, can be confirmed simply by viewing the protruded end of the catheter member 11 through the endoscopic observation window 5. This permits to check the ultrasound scan position in a considerably facilitated manner and to locate and operate the ultrasound transducer 21 correctly in a position facing a target intracorporeal portion of ultrasound examination, contributing to improve the operational maneuverability of the ultrasound probe to a marked degree.

The flexible transmission shaft 23, which is constituted by transmission coil or coils in the form of a series of tightly contacting helices as described hereinbefore, can be stretched into a tensioned state when mounting same within the sheathing tube 20. However, the stretching of the coils could impair the tightness of contact between the adjacent helices of the coil. However, even if stretched in a tensioned state, the flexible shaft 23 can transmit the rotation to the ultrasound transducer 21 substantially free of a play as long as the incremental length by the stretching is less than 1%, inclusive, of the overall length of the flexible transmission shaft 23. Nevertheless, a relatively weak pressing force is exerted on the end face of the rotatable support member 22 which is abutted against the stopper ring 35 as well as on the shoulders of the rotary barrel member 26 which are abutted against the connecting shell member 31. Therefore, it is necessary to reduce the friction of sliding contact at these abutted portions to a minimum level. For this purpose, the connecting shell 31 and the stopper ring 35, which serve as rear and front stoppers for the flexible transmission shaft 23, are formed of a metal and finished to have a smooth surface on the abutting end faces 31a and 35a, respectively. On the other hand, the rotatable support member 22 and the rotary barrel member 26 are formed of a synthetic resin material of slippery low friction properties and likewise finished to have a smooth surface on their abutting end faces 22a and 26a, respectively. As the flexible transmission shaft 23 is held in sliding contact with the stopper means through these smoothly finished surfaces of metal and synthetic resin material, it can be put in smooth rotation to transmit the rotation accurately to the ultrasound transducer 21 on the rotatable support member 22 free of irregular fluttering motions in rotation.

Although both of the connecting shell member 31 and stopper ring 35 are made of a metallic material, the stopper ring 35 is electrically shielded off by the flexible sheathing tube 20 while the connecting shell 31 is shielded on its inner and outer sides by the rotary barrel member 26, sleeve 29 and outer shell 30 of synthetic resin material together with the rubber sleeve 32 which is extended over the connecting shell 31. Therefore, electrical accidents such as electrical leaks are suitably precluded to safeguard the patient even in the event of breakage of or damage to the insulating coating of the signal cable 24.

What is claimed is:

1. A catheter type ultrasound probe including an elongated flexible catheter member having an ultrasound transducer mounted on a tip end portion thereof and a controller having a rotational drive means for said ultrasound transducer, said catheter member comprising:

a flexible sheathing tube closed with an acoustic end cap at the distal end thereof through an annular stopper ring;

a rotatable support member located within said acoustic end cap at the distal end of said sheathing tube;

an ultrasound transducer mounted on said rotatable support member;

a flexible transmission shaft constituted by at least a transmission coil consisting of a series of intimately contacting helices, said flexible transmission shaft being extended through said flexible sheathing tube and connected at the fore end thereof to said rotatable support member;

a rotational shaft coupled with the rear end of said flexible transmission shaft and rotationally driven from said rotational drive means on said controller; and fore and rear stopper means located in fore and rear end portions of said catheter member to retain the flexible transmission shaft in tensioned state between predetermined head and tail end positions of said catheter member, said fore stopper means being constituted by an annular stopper surface formed on the inner periphery of said stopper ring and abutted against a proximal end face of said rotatable support member for sliding contact therewith.

2. A catheter type ultrasound probe as defined in claim 1, wherein said rear stopper member is constituted by a generally cylindrical shell member connected to the proximal end of said flexible sheathing tube and held in sliding contact with said rotational shaft.

3. A catheter type ultrasound probe as defined in claim 2, wherein said rotatable support member and said shell member are formed of an electrically insulating synthetic resin material.

4. A catheter type ultrasound probe as defined in claim 1, said rotational shaft is detachably connectible to said rotational drive source on said controller.

* * * * *